United States Patent [19]

Witz et al.

[11] 3,959,081

[45] May 25, 1976

[54] RAPID IDENTIFICATION OF BACTERIA USING CHEMILUMINESCENCE

[75] Inventors: Samuel Witz; Walter H. Hartung, both of Los Angeles, Calif.

[73] Assignee: Akzona Incorporated, Asheville, N.C.

[22] Filed: Mar. 26, 1975

[21] Appl. No.: 562,068

[52] U.S. Cl. ........................... 195/103.5 R
[51] Int. Cl.² ........................... C12K 1/04
[58] Field of Search ............. 195/103.5 R

[56] References Cited
UNITED STATES PATENTS 3,564,588  2/1971  Soli ..................... 195/103.5 R
3,797,999  3/1974  Witz et al. ............. 195/103.5 R Primary Examiner—A. Louis Monacell
Assistant Examiner—Robert J. Warden
Attorney, Agent, or Firm—Francis W. Young; Philip M. Pippenger

[57] ABSTRACT

A method for identifying a heme-containing microorganism species through the addition of luminol and hydrogen peroxide to a suspension of the microorganism species, thus causing a light emission, accompanied by a recording of the build-up and decay of the light emission which provides a characteristic curve indicative of the microorganism species of the suspension.

10 Claims, 10 Drawing Figures

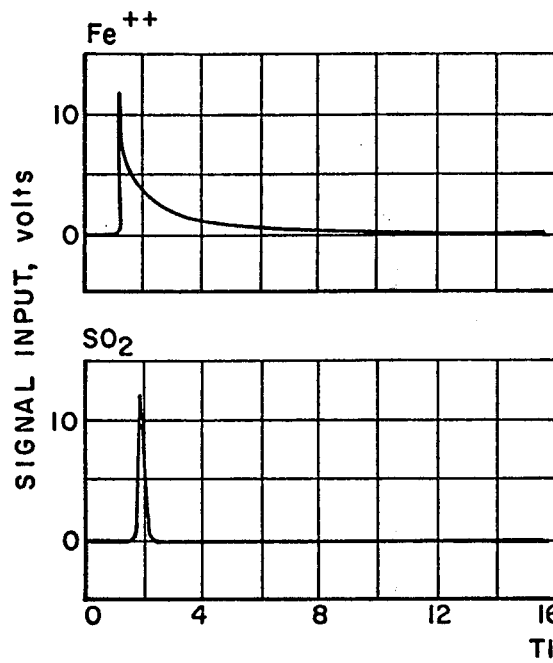
FIG. 3a
FIG. 3b
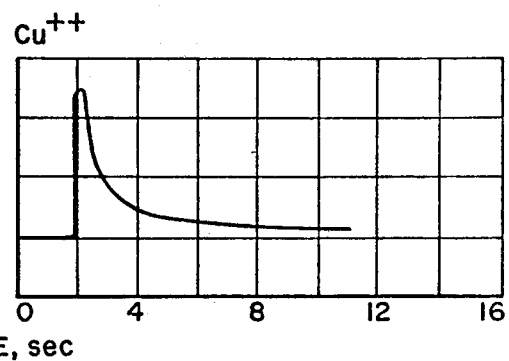
FIG. 3c
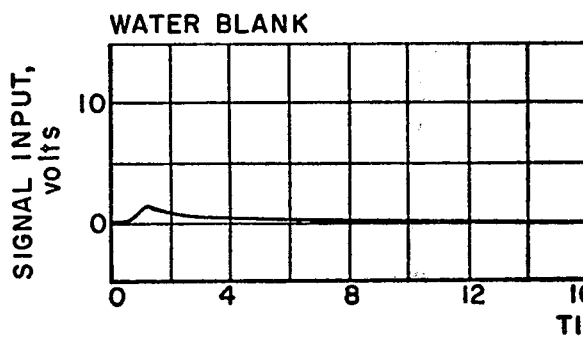
FIG. 4a
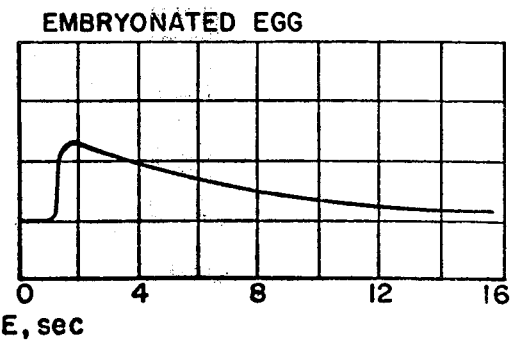
FIG. 4b

3,959,081

RAPID IDENTIFICATION OF BACTERIA USING CHEMILUMINESCENCE

THE INVENTION

The present invention relates to a process for identifying species of various biological microorganism including bacteria and fungi which microorganism contain a hemoprotein substance containing an iron porphyrin prosthetic group, such as, catalase or the cytochromes. The method makes use of the well-known light reaction of luminol in the presence of peroxide and utilizes the known ability of heme materials to initiate the chemiluminescence. Prior art methods including Soli, U.S. Pat. No. 3,564,588 have recognized and utilized the light reaction of luminol and hydrogen peroxide, together with the ability of microorganisms to decompose the peroxide through the enzyme catalase. Soli has used the foregoing chemiluminescent system for the detection of living organisms and thereby to differentiate the living organisms from inert matter. He has shown that various groups of organisms have differing degrees of catalase activity, but he does not recognize that the light emission curve of each species has a characteristic light build-up and decay. It is crucial to Soli's process that there be initially a sustained light reaction provided by the peroxide and luminol before adding thereto the sample solution containing a suspected living microorganism. If the added solution does contain a living microorganism, Soli reports that there will be a noticeable decay in the light reaction, which drop in light intensity in the practice of his process is interpreted to reveal the presence of living microorganisms.

With the process of the invention while utilizing essentially the same chemistry, it is possible to define specific micoorganisms and this is achieved by recording the light emission including at least a portion of the light build-up and decay to thus provide a characteristic time curve which it has been found is distinctive of each microorganism. In the preferred embodiment, the complete light build-up as well as decay of the light emission is recorded; however, it has been noted that in most instances, it is possible to make an identification of a microorganism species by recording only a portion of the light build-up and decay curve. It has been found that certain non-biological agents which may be present in the suspension, e.g., $Fe^{++}$, $Cu^{++}$ and $SO_2$ do initiate luminescence and have light emission characteristics which, fortuitously, are markedly different from most biological agents. The light emission curves of the foregoing named inorganic agents terminate in less than about one second and since the time to reach maximum luminescence of most microorganisms of interest exceeds one second, typically 5–8 seconds and longer, it is possible to record only a portion of the light emission curve of the microorganisms of interest and thus avoid noise background of the inorganic agent.

Other objects and advantages of the invention will become apparent from the following description when considered in conjunction with the accompanying drawings wherein:

FIG. 2b is a graph based on a photograph of a oscilloscope trace illustrating the light emission curve of a chemiluminescent reaction of a suspension containing *S. marcescens* at a concentration of $2.6 \times 10^5$ cells/ml with the same graph coordinate units as in FIG. 2a;

FIG. 2c is a graph based on a photograph of an osciloscope trace illustrating the light emission curve of a chemiluminescent reaction of a suspension containing *E. coli* at a concentration of $4.1 \times 10^4$ cells/ml with the same graph coordinate units as in FIG. 2a;

FIG. 2d is a graph based on a photograph of an osciloscope trace illustrating the light emission curve of a chemiluminescent reaction of a suspension containing *B. cereus* at a concentration of $2.5 \times 10^4$ cells/ml with the same graph coordinate units as in FIG. 2a;

FIG. 3a is a graph based on a photograph of an osciloscope trace illustrating the light emission curve of a chemiluminescent reaction of a suspension containing $Fe^{++}$ (70 ppb) with the abscissa being expressed in seconds and the ordinate in volts;

FIG. 3b is a graph based on a photograph of an osciloscope trace illustrating the light emission curve of a chemiluminescent reaction of a suspension containing $SO_2$ with the same graph coordinate units as in FIG. 3a;

FIG. 3c is a graph based on a photograph of an osciloscope trace illustrating the light emission curve of a chemiluminescent reaction of a suspension containing $Cu^{++}$ (1.5 ppm) with the same graph coordinate units as in FIG. 3a;

FIG. 4a is a graph based on a photograph of an osciloscope trace illustrating the light emission curve of a chemiluminescent reaction of a suspension containing water blank with the abscissa being expressed in seconds and the ordinate in volts; and FIG. 4b is a graph based on a photograph of an oscilloscope trace illustrating the light emission curve of a chemiluminescent reaction of a suspension containing embryonated egg with the same graph coordinate units as in FIG. 4a.

Figure 1:
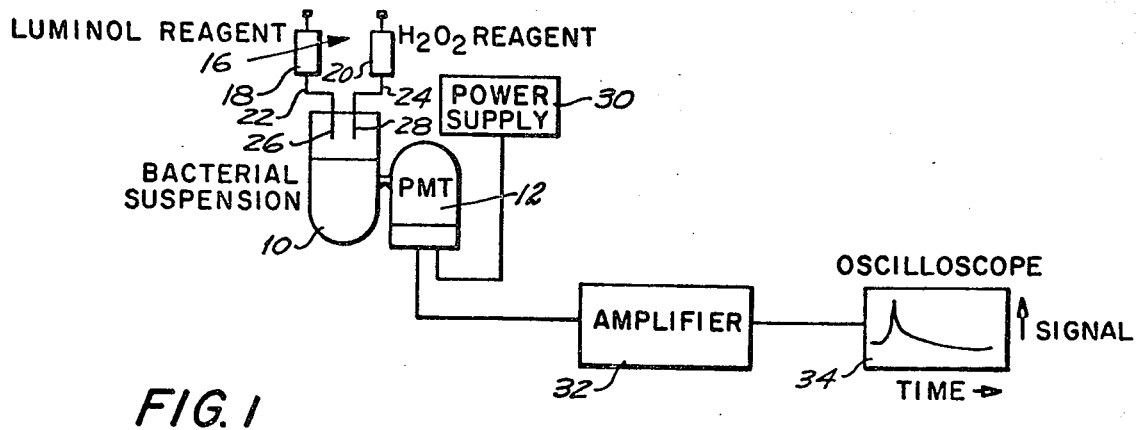
FIG. 1 is a diagramatic representation of a preferred embodiment of a system for the practice of the process of the invention.

The graphs of several figures show the rate of luminescent build-up and decay obtained by simultaneously injecting 0.2 ml each of luminol reagent and $H_2O_2$ reagent into a test tube containing a one ml aqueous suspension of the agent indicated. The light utput was monitored by an RCA 1P21 photomultiplier tube and a Tektronix Type 541A oscilloscope. A preferred embodiment of a system generally like that used in gathering the data for the graphs of the several figures is illustrated in FIG. 1, wherein there is illustrated a reaction cell 10 adjacent a photomultiplier tube 12. Generally, the two units will be enclosed in a light-proof enclosure. Means 16 is provided for separately and simultaneously injecting the luminol reagent and the $H_2O_2$ reagent into the reaction chamber 10. In the particular embodiment illustrated, the injection means 16 takes the form of two spring-loaded syringes 18 and 20 which are connected respectively by lines 22 and 24 to injection nozzles 26 and 28 which are spaced somewhat above the liquid level of the microorganism water suspension. The liquid reagents in being injected into the contents of the cell 10 are assured of turbulent and substantially instantaneous mixing.

Figure 2A:
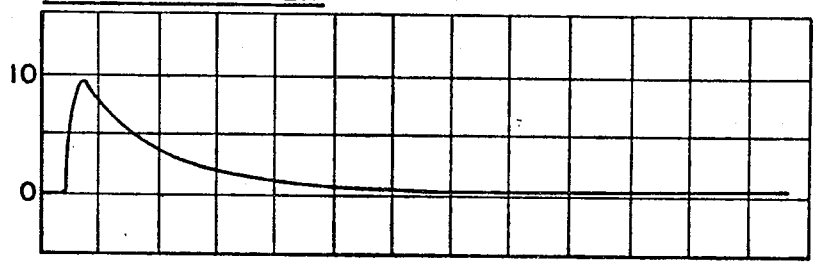
FIG. 2a is a graph based on a photograph of an osciloscrope trace illustrating the light emission curve of a chemiluminescent reaction of a suspension containing *Aspergillus niger* at a concentration of $3.7 \times 10^3$ cells/ml with the abscissa being expressed in seconds and the ordinate in volts.
Figure 2B:
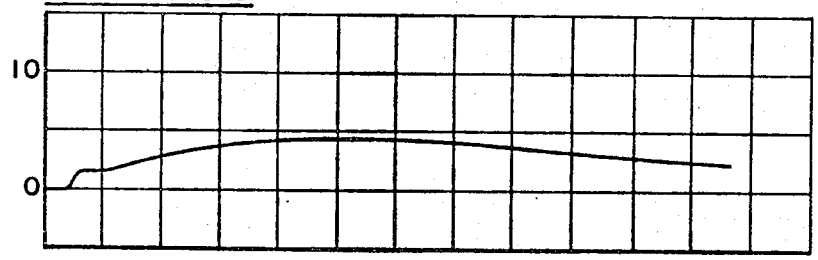
Figure 2C:
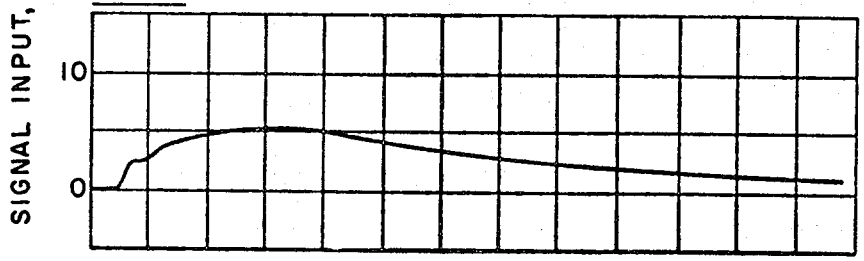
Figure 2D:
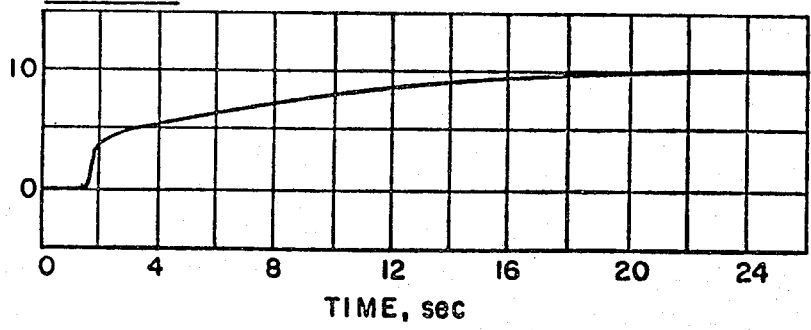

It will be appreciated that known means may be utilized for simultaneously accomplishing the luminol and peroxide injections. The photomultiplier tube 12 is energized by a power supply 30 with the output of the photomultiplier tube being connected to an amplifier 32 which, in turn, is coupled to an oscilloscope 34. In collecting the data used in the several graphs, a photograph was taken of the oscilloscope traces by a camera (not illustrated). In some instances, such as in the tests collecting the data for FIGS. 2b and 3c, the shutter of the camera taking the photograph was arbitrarily closed before the oscilloscope trace had reached the base line because the time interval had grown excessively long and further recording of the light decay was unnecessary since a distinctive portion of the light curve for the particular species had already been obtained.

The luminol reagent was typically prepared by dissolving 0.33 grams luminol, 5.00 grams EDTA (disodium ethylenediaminetetracetic acid) and 20.00 grams NaOH in one liter of double distilled water. The purpose of the NaOH in the formulation is to give the preferred alkalinity (pH 11) so as to provide the optimum quantum yield for the reaction. It has been observed that the light output drops off markedly with a pH below 10.5. The EDTA complexes with the trace metal ions that may be in solution which, if present, would otherwise contribute to the light output.

The $H_2O_2$ reagent comprises 0.5% $H_2O_2$ in distilled water with 0.0002% of acetrophenetidin which latter material is a preservative of the hydrogen peroxide. For maximum sensitivity, the concentrations of the ingredients of the luminol and $H_2O$ reagents are desirably maintained within 10% of those indicated. It will be appreciated that in the test reported in FIGS. 3a and 3c, that the luminol reagent contained no ETDA.

There are three general types of behavior indicated by the various agents whose time curves are recorded in the several Figures. The three general types are summarized in the table below.

*niger* requiring 0.4 to 0.8 sec. to reach a maxium and 3 to 6 sec. to decay to 50% of peak luminescence.

The non-biological initiators, i.e., metal salts such as $Fe^{++}$, $Cu^{++}$ and oxidants such as $SO_2$ (it is believed that $NO_2$, $Cl_2$, and $O_3$ behave similarly) exhibit a sharp rise and decay (maximum in 0.2 sec. or less and decay to 50% peak luminescence in 0.2 to 0.6 seconds).

The mechanism that accounts for these differences is not fully understood at the present time. For the biological agents, part of the difference may be due to the rate at which the reagents are able to permeate the cell wall and/or the availability of the hematin (i.e., extent of protein denaturation required to reach the heme moiety).

Somewhat differing concentrations of the same bacterial species do not objectionably alter the characteristic shape of the luminescent build-up and curve and for a selected set of conditions including temperature and concentration of the species in the aqueous suspension, the light emission curve for a particular organism is fully reproducible. It has been demonstrated that it is best to avoid either pretreatment of the biological agent suspension with luminol or heating of the bacteria, say to 60° to 70° C. for two minutes as either manner of pretreatment will change the distinctive shape of the emission curve so as to require a different comparative curve for identification purposes. There is a tendency for such pretreatments to shift the maximum luminescence of the curve into a time sector which would be interfered with by metal ions if such be present in the test suspension. However, it has been demonstrated that heating the bacterial suspension to 53° C. for 30 seconds does not appear to alter to an objectionable degree, the shape of the emission curve so as to cause the profile of the curve to significantly depart from its characteristic shape.

Flow conditions, e.g., the rapidity with which the

| Agent | Concentration, cells/ml | Time to Max. Lum., sec. | Time to Decay to 50%, sec. | Time to Decay to 20%, sec. |
|---|---|---|---|---|
| S. marcescens | $(2.6 \times 10^5)$ | 8 | 21–24 | — |
| E. Coli | $(4.1 \times 10^4)$ | 5 | 13 | 29 |
| B. cereus | $(8 \times 10^3$ to $2.5 \times 10^4)$ | 16–24 | >30 | — |
| Embryonated Egg | — | 0.4 | 3–6 | 6–10 |
| Aspergillus niger | $(3.7 \times 10^2$ to $3.7 \times 10^3)$ | 0.4 | 1.5–3 | 8 |
| $Fe^{++}$ | (70 ppb) | 0.2 | 0.4 | 0.8 |
| $Cu^{++}$ | (1.5 ppm) | <0.2 | 0.6 | 2 |
| $SO_2$ | — | <0.2 | <0.2 | <0.2 |
| Reagent Blank | — | 0.4 | 1 | — |

As illustrated in the table and which can be confirmed with reference to the figures, organisms, such as, *S. marcescens*, *E. coli* and *B. cereus* spores require 5 seconds or longer to reach maximum luminescence and about 13 seconds or longer to decay to 50% of peak value. Among the biological agents, the other extreme is represented by *Aspergillus niger* spores (spore diameter of about 5 $\mu$). These fungi might be considered typical of the mold spores constituting the major biological interference in ambient atmosphere testing where practiced. This agent exhibits a rapid rise (~0.4 sec. to maximum) as well as a rapid decay (decay to 50% of peak in 1.5 to 3 sec.). The curve of embryonated egg, is shifted somewhat to the right of the *Asp.* mixing of the reagents and the bacterial suspension is accomplished, shape of the reaction cell, significant variations in concentrations of the bacterial suspension, temperatures, concentrations of the reagents have varying effects upon the shape of the time-luminescent curve and it may be said that generally speaking, minor departures in the foregoing variables will not objectionably change the characteristic shape of the curve. There are a number of sets of variables which produce species curves of distinctive characteristics which may be employed for microorganisms identification.

Therefore, it will be appreciated that in any given system, once the variables are settled upon and the acceptable variations therefrom defined that there will be a set of characteristic species curves available for identification of various biological microorganisms. In the detection of some organisms such as *E. coli* or *S. marcescens* against an interferring background signal, monitoring of the light output may be commenced three seconds or so after addition of the hydrogen peroxide and luminol reagents and such time lapse will assure a maximum signal-to-noise ratio (i.e., there will be substantial elimination of the background interference of metal salts or oxidizing gases). Other organisms may require a different time elapse for maximum signal-to-noise ratio.

As seen in the table above, the interference of embryonated egg may be generally eliminated by commencing monitoring of the light input after a lapse of 3 to 6 seconds and still obtain a characteristic signal. Background noise attributable to *Aspergillus niger* and similar background particulates may be significantly avoided by delaying monitoring for 1.5 to 6 seconds.

We claim:

1. A method of identifying an individual heme-containing microorganism species, utilizing luminol and hydrogen peroxide as reagents, said method comprising:
   a. bringing the luminol and hydrogen peroxide together in the presence of a suspension of the microorganism species to be identified and thereby causing a light emission;
   b. recording the light emission including at least a portion of the light build-up and decay to thus provide a characteristic time curve;
   c. comparing the characteristic time curve obtained in step (b) with known time curves for said individual microorganism species;
   d. whereby the record of said characteristic curve is indicative of the microorganism species of the suspension.

2. A method in accordance with claim 1 wherein the recording of the light emission curve begins with the bringing together of the luminol and hydrogen peroxide in the suspension.

3. A method in accordance with claim 1 wherein the recording of the light emission curve in step (b) is commenced after a brief interval of time of less than about one second following the bringing together of the luminol and hydrogen peroxide to permit differentiation of microorganism species signals from background interference signals.

4. A method in accordance with claim 3 wherein the light recording is commenced about 0.6 seconds after bringing together of the luminol and hydrogen peroxide to permit differentiation of light caused by metal ions possibly present in the suspension.

5. A method in accordance with claim 1 wherein the recording is commenced after bringing together of the luminol and hydrogen peroxide and an elapse of time permitting substantial decay of light caused by *Aspergillus niger* and similar fungi possibly present in the suspension to maximize the signal-to-noise ratio.

6. A method for identifying an individual heme-containing microorganism species, said method comprising:
   a. providing said microorganism species in an aqueous suspension;
   b. separately and simultaneously supplying luminol and hydrogen peroxide under pressure to the suspension, thus assuring turbulent mixing and the immediate provision of light emission;
   c. recording the light emission including at least a portion of the light build-up and decay to thus provide a characteristic time curve;
   d. comparing the characteristic time curve obtained in step (c) with known time curves for said individual microorganism species;
   e. whereby the record of said characteristic curve is indicative of the microorganism species of the suspension.

7. A method in accordance with claim 6 wherein the recording of the light emission curve begins with the addition of the luminol and hydrogen peroxide to the microorganism suspension.

8. A method in accordance with claim 6 wherein the recording of the light emission curve in step (c) is commenced after a brief interval of time of less than about one second following the bringing together of the luminol and hydrogen peroxide to permit differentiation of microorganism species signals from background interference signals.

9. A method in accordance with claim 8 wherein the light recording is commenced about 0.6 seconds after bringing together of the luminol and hydrogen peroxide to permit differentiation of light caused by metal ions possibly present in the suspension.

10. A method in accordance with claim 6 wherein the recording is commenced after bringing together of the luminol and hydrogen peroxide and an elapse of time permitting substantial decay of light caused by *Aspergillus niger* and similar fungi possibly present in the suspension to maximize the signal-to-noise ratio.

* * * * *